United States Patent [19]

Albainy et al.

[11] 4,170,226
[45] Oct. 9, 1979

[54] DIGITAL SPHYGMOMANOMETER

[76] Inventors: Bolivar Albainy, 8408 Sierra Oval, Parma, Ohio 44130; Alexis E. Khoury, 11 Spring St., Danielson, Conn. 06239

[21] Appl. No.: 819,488

[22] Filed: Jul. 27, 1977

[51] Int. Cl.² .............................................. A61B 5/02
[52] U.S. Cl. ..................................... 128/667; 128/681
[58] Field of Search ................. 128/2.05 A, 2.05 M, 128/2.05 F, 2.05 G, 2.05 Q

[56] References Cited

U.S. PATENT DOCUMENTS

| 3,056,401 | 10/1962 | Greenspan et al. | 128/2.05 M X |
| 3,348,534 | 10/1967 | Marx et al. | 128/2.05 M |
| 3,480,005 | 11/1969 | Edwards | 128/2.05 M |
| 3,552,381 | 1/1971 | Burns et al. | 128/2.05 A |
| 3,915,156 | 10/1975 | Wastl et al. | 128/2.05 Q X |
| 3,978,848 | 9/1976 | Yen et al. | 128/2.05 M |

*Primary Examiner*—Lee S. Cohen
*Attorney, Agent, or Firm*—Maky, Renner, Otto & Boisselle

[57] ABSTRACT

A digital sphygmomanometer is disclosed in which a conventional arm cuff and a compact high sensitivity pneumatic sensor measuring system utilizing mechanical/optical/electronic techniques rapidly and accurately converts one's own or a patient's blood pressure to encoded digital signals which provide dual latched three digit displays of systolic and diastolic pressures with countdown in 1 mm Hg increments on the respective displays of cuff pressure as it is decreased to systolic pressure and as it is decreased from systolic to diastolic pressure.

4 Claims, 6 Drawing Figures

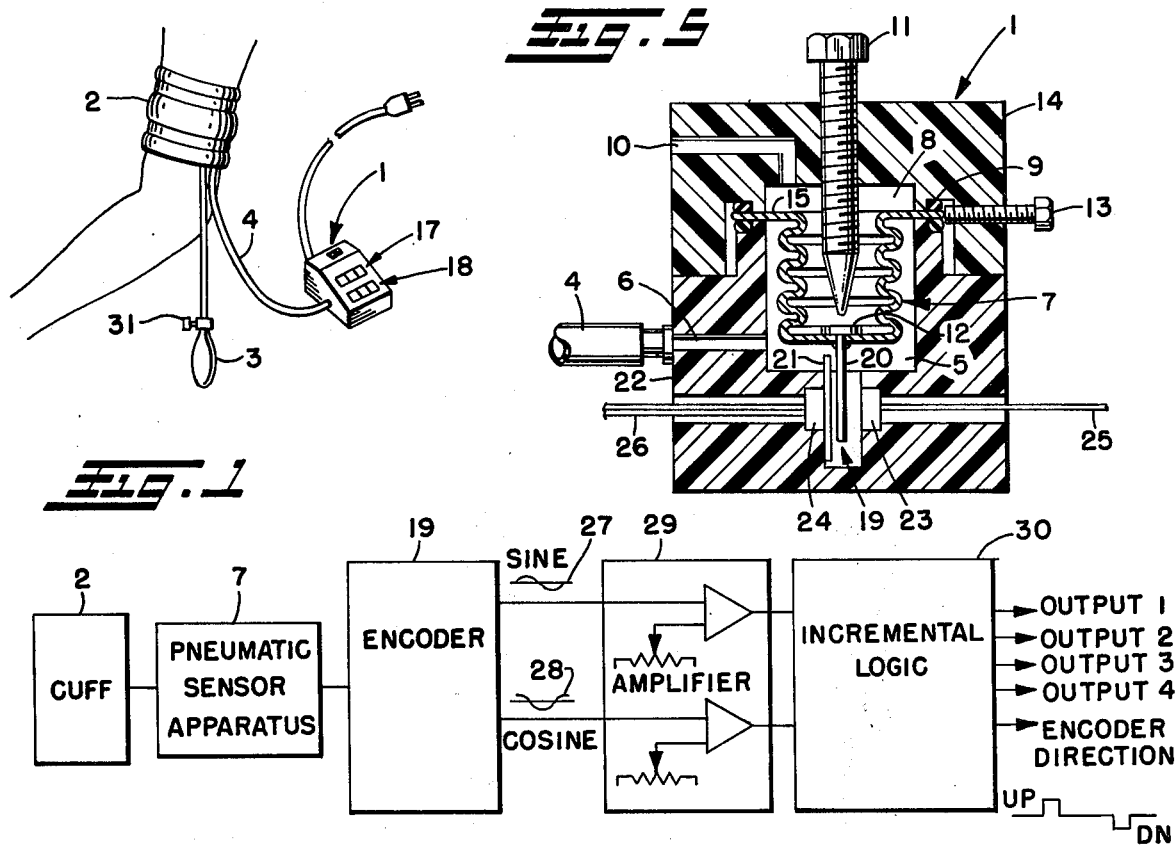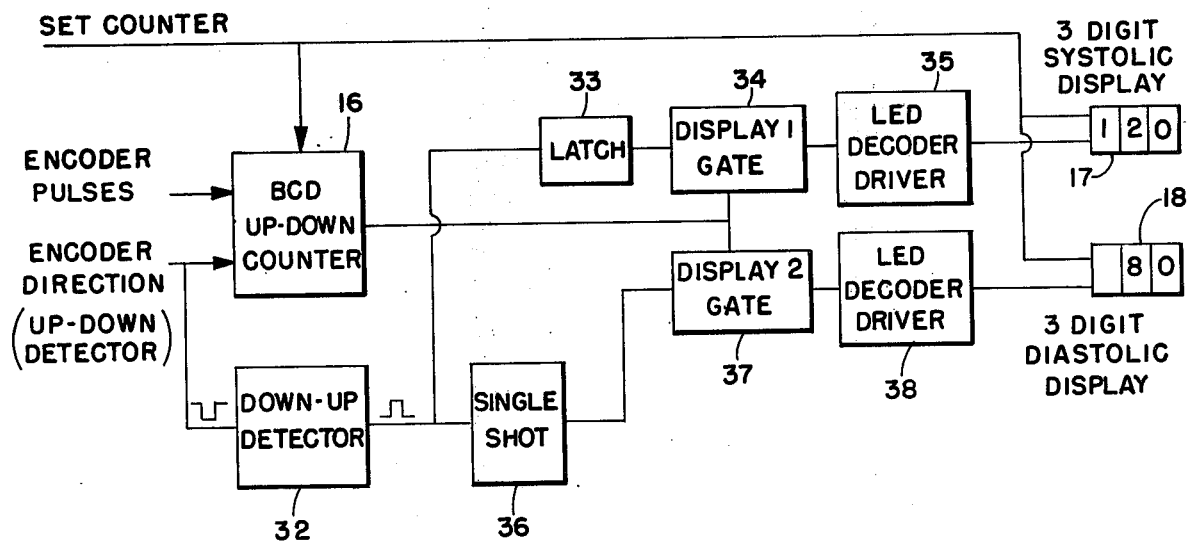

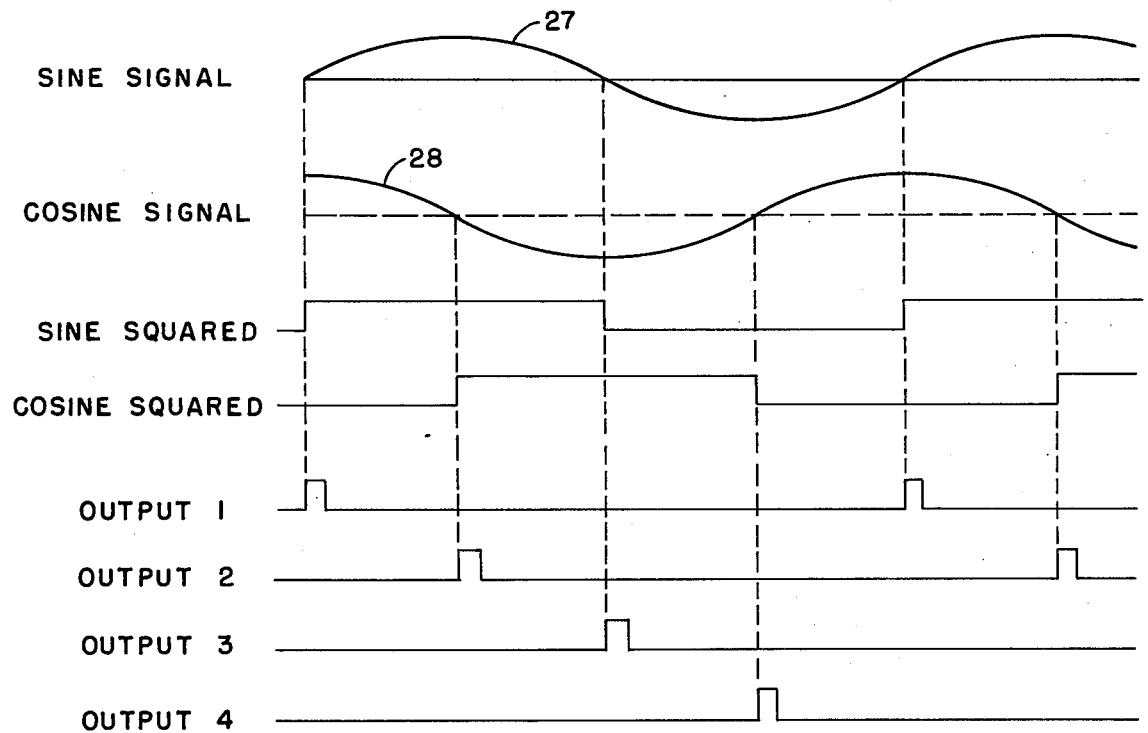
_Fig. 4_
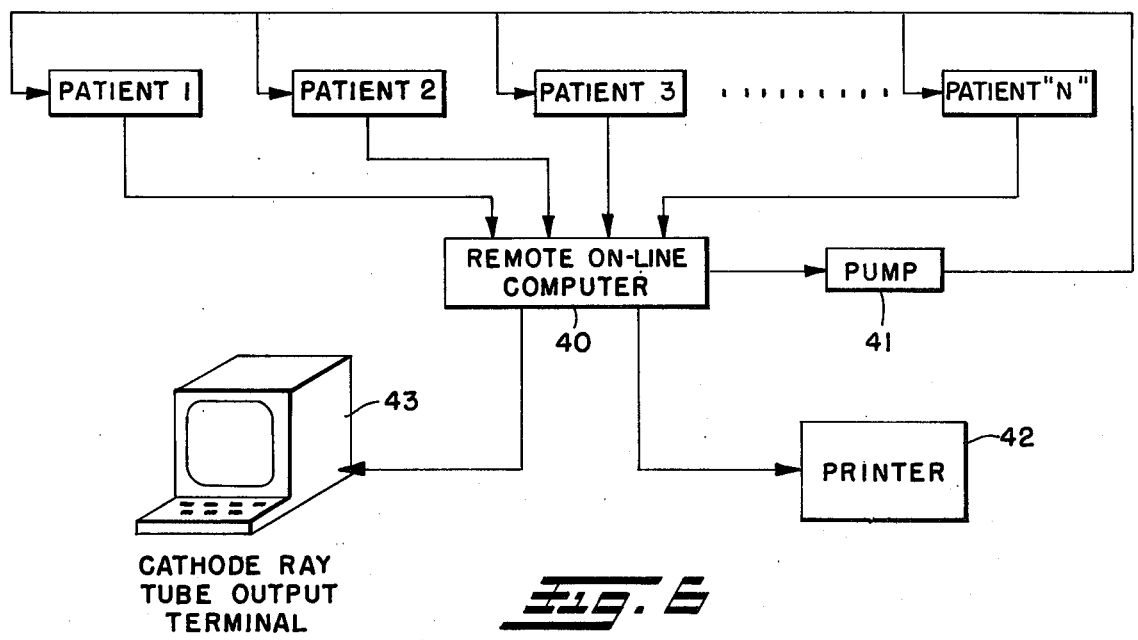
_Fig. 6_

DIGITAL SPHYGMOMANOMETER

BACKGROUND OF THE INVENTION

In order to take blood pressure it is conventional practice for a doctor (or nurse or other trained operator) to wrap the cuff of a sphygmomanometer around a patient's arm. He then utilizes one hand to inflate the cuff by means of a squeeze bulb to impede the flow of blood to the arm, while with his other hand he holds the sensor of a stethoscope on the patient's arm to monitor heart pulses acoustically. Using his first hand, the doctor then slowly bleeds air from the cuff to gradually decrease the pressure in the cuff while carefully observing the pressure gauge (aneroid or mercury column) of the sphygmomanometer. As the pressure in the cuff decreases he observes and mentally retains the pressure gauge readings at which the first heart pulse is heard (systolic pressure) and at which the heart pulses cease to be heard (diastolic pressure). It is common for the doctor or operator to repeat this process one or more times either to confirm the initial readings in the event that he may not have been able to clearly detect the systolic and diastolic pressure points, or to minimize the ambiguity of this type of measuring system, or to average the results, or to re-affirm the results in the event of loss of trend of concentration or failure to recall one or both of the observed readings.

It is also clear that owing to the inherent lack of precision with this type of medical measurement system, the results vary significantly from operator to operator. Additionally, as conventionally configured and utilized, this instrument is slow, necessitates much subjective judgement in interpreting the results, is cumbersome to use, and does not easily adapt itself for use by an average patient in taking his own blood pressure.

SUMMARY OF THE INVENTION

The digital sphygmomanometer herein, in conjunction with an inflatable arm cuff, pump, and bleed valve provides a cuff pressure sensor which through optical and electronic devices transforms decreasing cuff pressure into three digit systolic and diastolic pressure readouts in mm. of Hg with countdown to systolic pressure on the systolic readout and with countdown from systolic pressure to diastolic pressure on the diastolic readout.

A principal object of the present invention is to provide an apparatus and method for automatically measuring blood pressure without the need for conventional manometers or stethoscopes.

Another object of this invention is to provide a simple apparatus which is easy to set up and use by an operator or by the patient himself to rapidly and accurately monitor blood pressure independently of operator or patient skill and without requiring operator or patient judgement on the interpretation of the results.

Other objects and advantages will appear from the ensuing description.

BRIEF DESCRIPTION OF THE DRAWING

FIG. 1 is a perspective view showing the digital syphgmomanometer herein in use;

FIGS. 2 and 3 are schematic diagrams showing successive components of the present invention from the cuff to the incremental logic device (FIG. 2), and from the up-down counter and down-up detector which receive the encoder output pulses and encoder direction pulses to the systolic and diastolic displays (FIG. 3);

FIG. 4 depicts the sine/cosine wave pattern output of the encoder, the signal shaping, and the sequential encoder pulse outputs as a function of encoder displacment;

FIG. 5 is a cross-section view of the pneumatic sensor and encoder portions of the present invention; and FIG. 6 is a block diagram illustrating a system for concurrent automatic multi-monitoring of blood pressure data of numerous patients.

DETAILED DESCRIPTION OF A PREFERRED EMBODIMENT

Referring now to the drawings, and especially to FIGS. 1 and 5, apparatus 1 automatically detects and records blood pressure from a conventional inflatable cuff 2. The cuff 2 is wrapped around the patient's arm and is pumped up or inflated by means of hand pump or squeeze bulb 3. The cuff pressure is transmitted by means of a flexible tube 4 into cavity 5 of apparatus 1 through pressure port 6. A pneumatic sensor in the form of a metal bellows 7 deflects upward against its own natural spring constant as a result of the force created by the air pressure unbalance existing between cavity 5 and cavity 8. Cavities 5 and 8 are isolated from each other by means of the bellows 7 and the O-rings 9. Cavity 8 is vented to atmosphere through vent port 10.

The cuff pressure and, consequently, the pressure in cavity 5 is increased by pump 3 until the bellows 7 contacts the adjustable terminal post 11. At that point an electrical circuit is completed comprising contact post 11, metal disk 12 brazed to the conducting bellows 7, and contact post 13 which extends through the non-conducting pneumatic sensor block 14 to contact bellows 7 at the peripheral of the flange 15 thereof. This signal may be used: (1) to indicate to the operator that he may stop pumping cuff 2 because he has gone beyond the expected systolic pressure, and (2) to set or initialize the up-down counter 16 and systolic and diastolic displays, 17 and 18, shown in block diagram in FIG. 3. The bellows 7 spring rate and diameter is chosen to correspond to a predetermined blood pressure, say 170 mm of Hg, when the electrical circuit described is completed. Adjustable screw post 11 can be further used to calibrate the apparatus initially to compensate for manufacturing tolerance variations in the bellows spring rate. Calibration can be achieved by externally setting the predetermined pressure in cavity 5 to say, 170 mm of Hg, and adjusting the post 11 until electrical contact is made with disk 12.

A preferred form of linear encoder 19 comprises a linear scale 20 which is attached to and moves with bellows 7, a reticle 21 which is fixed and attached to the pneumatic sensor block 22, dual light emitting diodes (LED) 23 which act as light sources, and dual photo-transistor cell detectors 24 which measure the linear deflection or position of the bellows 7 as it moves under the influence of the cuff pressure. Wires 25 are provided to power the LED light sources 23, and wires 26 are provided to pick up the bellows 7 position signals from the linear encoder photo-transistors 24. Thus, the encoder 19 is an optical/electronic measuring system which provides linear incremental encoding of position. Precision light weight Mylar or like plastic film strips constitute the scale 20 and reticle 21 with high resolution lines and spaces, photographically exposed, to produce encoder minimum count resolutions of say 500 microinches. The encoder 19 is implemented in this invention so that measurement of linear motion is accomplished by moving the linear scale 20 with respect to the stationary reticle 21 to produce a light and dark pattern as the collimated light from the light sources 23 passes through the fine graduations on the linear scale 20 and the fixed graduated reticle 21. This light and dark pattern is sensed by the pairs of photo cells 24 which are placed back to back to minimize DC offset and to enhance signal output.

As shown in FIG. 5, this compact encoder 19, equipped with cell 24 output, converts the linear bellows 7 motion into low level sine/cosine waves 27 and 28. The zero crossings of the sine/cosine waves are converted into digital signals for incremental counting. By assigning channel designations to both sine and cosine waves, a phase relationship is established for determining the direction of motion of the bellows 7. The low level sine/cosine encoder 19 signals are amplified by amplifier 29 and applied to an incremental logic circuit 30 which square off the waves and provide pulses in conventional quadrature output as illustrated in FIG. 4. The quadrature output is then processed logically, to provide up-down pulses as well as encoder direction signals.

The encoder 19 may be designed such that every 0.0005" motion of the bellows 7 corresponds to one digital encoder pulse; and the bellows 7 may be chosen so that, 1 mm of Hg pressure, corresponds to 0.0005" of bellows motion. Consequently, the sensitivity of apparatus 1 may be such that a cuff pressure of 1 mm of Hg corresponds to 1 digital encoder pulse, however, numerous other sensitivities are possible.

Once the set point pressure, of, say, 170 mm of Hg is achieved by the action of the hand pump 3, the operator now slowly opens bleed valve 31 allowing the pressure in the cuff 2 and, consequently, in cavity 5 to decrease. As the pressure decreases, bellows 7 starts deflecting downward as a result of its natural spring constant restoring force. Electrical contact is broken at the post 11 to metal disk 12 interface. This signal is used to set the counter 16 and the systolic and diastolic displays 17 and 18 to 170, corresponding to: (a) the pressure to which apparatus 1 was calibrated, and (b) the cuff 2 pressure at that instant of time. As the pressure continues to decrease, as a result of the continuously bleeding valve 31, a corresponding proportional bellows deflection and, consequently, encoder pulse train is generated. This encoder pulse train is fed to the up-down counter 16 illustrated in the logic block diagram, FIG. 3. The up-down counter starts to count down from 170, 1 count for every 1 mm of Hg pressure decrease. When the cuff pressure gets down to the point where blood just begins to flow downstream of the cuff 2 into the lower part of the arm, a slight pressure rise or pressure reversal is noted, this being the pulse that a doctor picks up acoustically with a stethoscope. This pressure rise is sensed by bellows 7 which suddenly and momentarily reverses direction and is deflected upward. This reversal in direction is logically detected by the incremental logic circuit 30 which provides a change in encoder direction signal. This signal is fed to the down-up count detector 32 which fires a single pulse signal to a latch 33. Latch 33 then gates through by means of display 1 gate 34, the address in counter 16, to a light emitting diode decoder driver 35. The decoder driver 35 decodes the binary coded decimal signal to decimal and sets the three digit display 17 with the systolic blood pressure. A similar action, through single shot device 36, sets the systolic blood pressure on the diastolic display 18 through display 2 gate 37 and decoder driver 38.

As the pressure continues to decrease the pressure reversals continue and are picked up by the down-up detector 32. The down-up detector continues to fire single pulses each and every time it senses a pressure reversal. However, while latch 33 remains latched, conserving the systolic pressure display 17 output, the diastolic display 18 continues to be updated as each down-up count reversal detection causes the new counter address to be dumped into the 3 digit diastolic display 18. Finally, when no more pressure reversals occur corresponding to when a doctor observes that the acoustic pulses cease to be heard with a stethoscope, the diastolic pressure display 18 is set. The operator now just reads the systolic and diastolic pressures from the displays 17 and 18.

In another embodiment, in lieu of utilizing the sudden changes of bellows direction, which correspond to the acoustic pulses the doctor picks up, to activate latch 33 and single shot 36 and, consequently, allowing the address in counter 16 to gate through, the acoustic pulses may be detected by means of an acoustic sensor or other similar device to act as the gating trigger.

The apparatus 1 described herein is of lightweight compact form approximately the same as a pocket size calculator with the two LED displays 17 and 18 indicating diastolic and systolic pressures. The apparatus 1 may be powered by batteries and/or alternating current.

Furthermore, by replacing the hand pump 3 with an automatic vacuum pump, and the bleed valve 31 with a solenoid operated bleed valve, the digital sphygmomanometer 1 may be made totally automatic. For example, a cuff 2 may be placed on a patient, and, on a regular interval of time, the automatic pump may be activated by means of an external control system (computer, stand-alone controller, etc.). When the pressure in the cuff 2 is sufficiently high, the bellows disk 12 contacts post 11, completing the electrical circuit from post 11 to post 13. An electrical signal may then be generated, which may be used to shut off the automatic pump and to open the solenoid operated bleed valve. Once the solenoid operated bleed valve is open the cuff pressure starts decreasing and the digital sphygmomanometer 1 operates as previously described; except now totally automatic.

Peripheral output devices, such as a printer or computer may also be integrated to the systolic/diastolic calculator. The systolic/diastolic pressures may be fed to these peripheral devices directly from the calculator. When fed to the computer in Binary Coded Decimal, the data may be further processed and computer diagnosed to alert a technician or nurse of complications.

It is also conceivable that the blood pressure of numerous patients may be automatically monitored simultaneously by placing a digital sphygmomanometer 1 on each patient and feeding the data directly to a control computer. This is shown diagrammatically in FIG. 6 wherein the blood pressure data of each of numerous patients is fed to a remote on-line computer 40 which automatically controls operation of pump 41 and a bleed valve (not shown in FIG. 6). The computer 40 collects and stores the blood pressure data from each patient in readable format and reports problems directly on an output printer 42 and/or an output terminal 43 such as a cathode ray tube output terminal.

The embodiments of the invention in which an exclusive property or privilege is claimed are defined as follows:

1. A digital sphygmomanometer comprising an inflatable cuff adapted to be wrapped around a patient's arm and having pump means and bleed valve means respectively operative to inflate said cuff to a pressure exceeding the expected systolic pressure of the patient and to bleed said cuff to gradually decrease the pressure therein; cuff pressure sensing means including a member exposed to the decreasing cuff pressure and movable linearly in one direction in proportion to the decreasing magnitude of the cuff pressure; digital systolic and diastolic pressure readout means; and transducer means for detecting reversal of movement of said member when cuff pressure decreases to just below patient's systolic pressure; latch means responsive to detection of such reversal by said transducer means for setting the patient's systolic pressure on said systolic pressure readout means; said transducer means including means for detecting cessation of pressure reversals when cuff pressure decreases to the patient's diastolic pressure; and further comprising means responsive to detection of such cessation by said transducer means for setting the patient's diastolic pressure on said diastolic pressure readout means.

2. The sphygmomanometer of claim 1 wherein said transducer means comprises encoder means operative in response to movement of said member to produce an electrical signal indicative of such movement; incremental logic means responsive to such signal for producing a pulse train representative thereof which is effective to actuate said systolic pressure readout means for countdown of cuff pressure as it is decreased to patient's systolic pressure, said incremental logic means having an output denoting encoder direction; and detector means responsive to such output denoting encoder direction for detecting a pressure reversal for actuating said latch means as aforesaid.

3. The sphygmomanometer of claim 2 wherein said detector means is further operative to set the patient's systolic pressure on said diastolic pressure readout means and to actuate said diastolic pressure readout means for digital countdown on said diastolic pressure readout means as the cuff pressure decreases from systolic pressure to diastolic pressure with pressure reversals; said detector means, upon cessation of said pressure reversals, being operative to set the diastolic pressure readout means to the patient's diastolic pressure.

4. The sphygmomanometer of claim 2 wherein said encoder means comprises a light source, a photocell to receive light energy from said source, a graduated scale secured to said member for movement therewith and a fixed graduated reticle, said scale and reticle being disposed between said light source and said photocell to alternately vary the intensity of light reaching said photocell to provide sine wave and cosine wave outputs of said photocell in predetermined phase relationship; said incremental logic means transforming said cosine and sine wave output to periodic pulses, and sensing the direction of movement of said member and scale to detect pressure reversals as occur when the patient's systolic pressure is reached and sensing the cessation of pressure reversals when the patient's diastolic pressure is reached.

* * * * *